United States Patent
Lane et al.

(10) Patent No.: US 12,336,921 B2
(45) Date of Patent: *Jun. 24, 2025

(54) STENT DEVICE HAVING REDUCED FORESHORTENING AND RECOIL AND METHOD OF MAKING SAME

(71) Applicant: ATRIUM MEDICAL CORPORATION, Merrimack, NH (US)

(72) Inventors: John Lane, Manchester, NH (US); David Heim, Portsmouth, NH (US); Christine Schick, Merrimack, NH (US); Jennifer Letzelter, Littleton, CO (US); Susan Hamelin, Dracut, MA (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/511,062

(22) Filed: Nov. 16, 2023

(65) Prior Publication Data

US 2024/0082024 A1    Mar. 14, 2024

Related U.S. Application Data

(60) Continuation of application No. 17/088,518, filed on Nov. 3, 2020, now Pat. No. 11,865,018, which is a
(Continued)

(51) Int. Cl.
*A61F 2/915* (2013.01)
*A61F 2/07* (2013.01)
*A61F 2/89* (2013.01)

(52) U.S. Cl.
CPC ............... *A61F 2/89* (2013.01); *A61F 2/07* (2013.01); *A61F 2/915* (2013.01);
(Continued)

(58) Field of Classification Search
CPC .... A61F 2/89; A61F 2/07; A61F 2/915; A61F 2002/072; A61F 2002/91541; A61F 2002/91583; Y10T 29/49826
See application file for complete search history.

(56) References Cited

U.S. PATENT DOCUMENTS

| | | | |
|---|---|---|---|
| 5,776,161 A * | 7/1998 | Globerman | A61F 2/915 D24/153 |
| 2004/0133271 A1* | 7/2004 | Jang | A61F 2/915 623/1.42 |

* cited by examiner

*Primary Examiner* — Suba Ganesan
(74) *Attorney, Agent, or Firm* — Fay Kaplun & Marcin, LLP (57) ABSTRACT

A stent device includes generally cylindrical rings aligned along a longitudinal axis, and interconnected by interconnecting members. Each interconnecting member includes a first coupling end, a second coupling end, and an elongate portion therebetween. The first coupling end, the elongate portion, and the second coupling end combine in either a first orientation or a second orientation, which are substantially mirror images. For each interconnecting member, the first coupling end can intersect with a midpoint of a transition region of a substantially repeating curved segment on one of the rings, and the second coupling end can intersect with a midpoint of a curved segment of a different and immediately adjacent ring. The interconnecting members can be arranged in rows extending longitudinally along the device. Along each row, consecutive interconnected members alternate between the first orientation and the second orientation. A cover may be provided over the stent device.

12 Claims, 7 Drawing Sheets

Related U.S. Application Data division of application No. 16/388,288, filed on Apr. 18, 2019, now Pat. No. 10,842,656, which is a continuation of application No. 13/834,250, filed on Mar. 15, 2013, now Pat. No. 10,271,975.

(52) U.S. Cl.
CPC .................. *A61F 2002/072* (2013.01); *A61F 2002/91541* (2013.01); *A61F 2002/91583* (2013.01); *Y10T 29/49826* (2015.01)

FIG. 4 (along line A-A)

STENT DEVICE HAVING REDUCED FORESHORTENING AND RECOIL AND METHOD OF MAKING SAME

CROSS-REFERENCE TO RELATED APPLICATION

This application is a Continuation of U.S. patent application Ser. No. 17/088,518 filed on Nov. 3, 2020, now U.S. Pat. No. 11,865,018; which is a Divisional of U.S. patent application Ser. No. 16/388,288 filed on Apr. 18, 2019, now U.S. Pat. No. 10,842,656; which is a Continuation of U.S. patent application Ser. No. 13/834,250 filed on Mar. 15, 2013, now U.S. Pat. No. 10,271,975. The disclosure of the above patent(s)/application(s) is incorporated herein by reference.

FIELD OF THE INVENTION

The present invention relates to expandable, intraluminal devices for use within a body passageway or duct. More particularly, the present invention relates to stent devices exhibiting substantially improved characteristics from known devices in the form of reduced foreshortening and recoil, and their methods of manufacture.

BACKGROUND OF THE INVENTION

A common method for treating stenosed vessels or other blocked passageways is to utilize an expandable prosthesis or stent. The stent is delivered to a target site, expanded, and affixed in place. The deployed and affixed stent creates an enlarged lumen space for passage of blood and also provides increased reinforcement of the vessel wall, in order to maintain the cleared passageway. Stents can be covered or uncovered. Some existing covered stents provide a series of interconnected metal rings encapsulated by a layer of biocompatible material. In uncovered stents (referred to as "bare metal stents"), the series of interconnected metal rings are exposed directly to the vessel and do not include any sort of cover.

Covered stents are desirable over bare metal stents in many circumstances as they provide more uniform coverage (e.g., gaps between stent struts are not exposed to walls of the target site, etc.) and improved luminal patency over bare metal stents in addition to other benefits. However, covered stents suffer from some operational shortcomings like foreshortening and recoil. In contrast, many bare metal stents exhibit little to no foreshortening and minimal recoil when deployed. Yet, the very same stents often will foreshorten by up to twenty five percent or more when deployed with a cover. However, in some instances, covered stents outperform bare metal stents in freedom from restenosis within particular defined periods of time (e.g., during the first 18 months following stent implantation).

Figure 1:
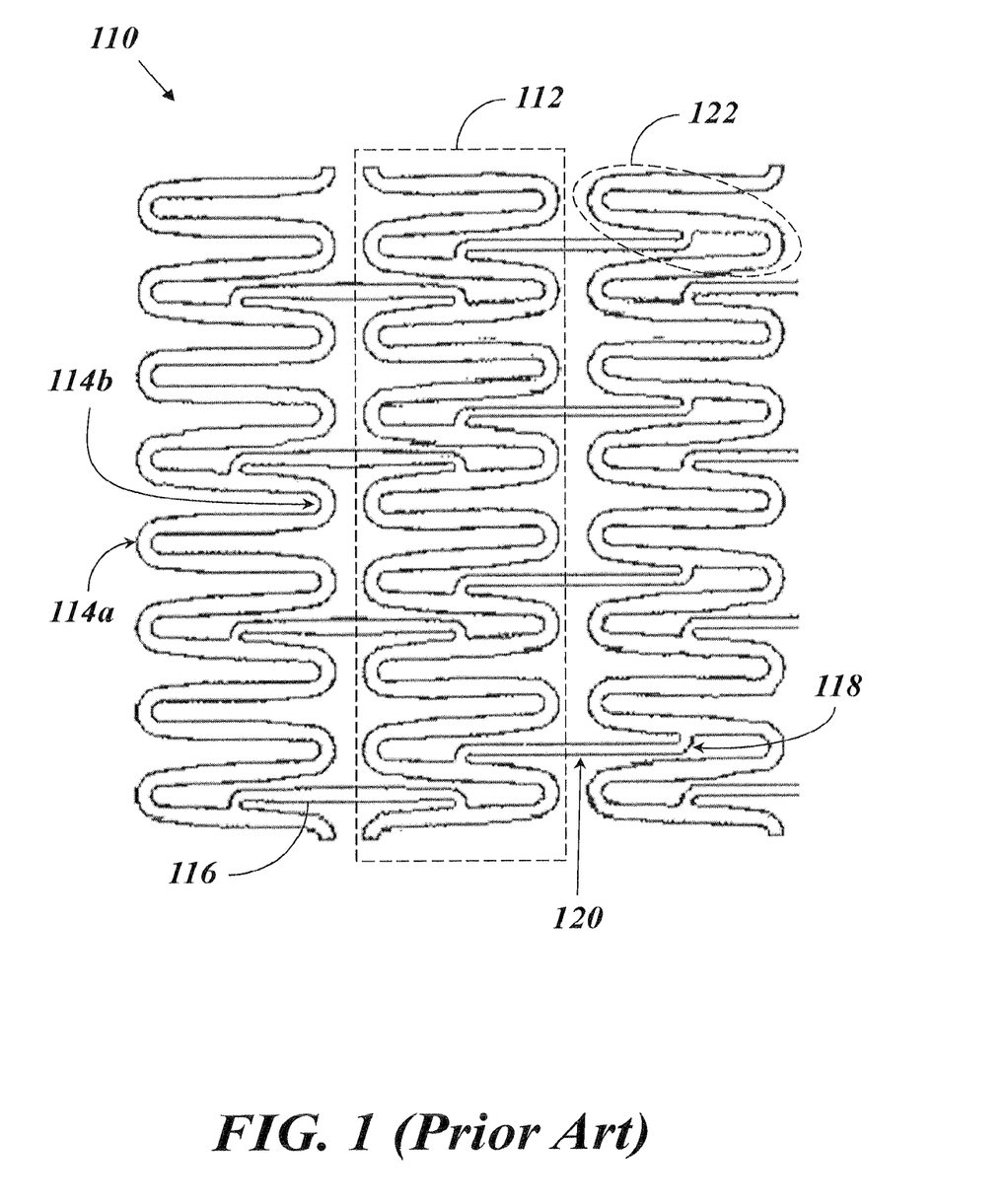
FIG. 1 is an illustrative diagram of a prior art stent.

For example, FIG. 1 depicts one example of a known stent design for a conventional covered stent 110 (cover not shown for clarity). The stent 110 is depicted in a flattened, discontinuous state for purposes of illustration. The stent 110 includes a series of rings 112, which in actuality are generally cylindrical and continuous at their ends (i.e., connected at the tops and bottoms). The rings 112 are generally cylindrical and aligned in a series. Each ring 112 is generally made up of a plurality of repeating peaks and valleys 114a, 114b. In the example stent 110 of FIG. 1, each particular ring 112 is a mirror image of any ring 112 adjacent to it in the series. Accordingly, for any two adjacent rings 112, the peaks 114a of one ring 112 are circumferentially aligned with the valleys 114b of the other ring 112, and vice versa. Each iteration of a peak 114a and a valley 114b forms a repeating bent segment 122. The rings 112 fixedly secured to one another by a plurality of interconnecting members 116. Each interconnecting member 116 includes two elbows 118 and an elongate portion 120 disposed therebetween.

In general, each interconnecting member 116 can occupy any one of a number of different configurations. In an "up-up" or "down-down" configuration, the elbows 118 of a single interconnecting member 116 extend to the same side (e.g., to the top or the bottom, respectively) of the elongate portion 120. Said differently, in an "up-up" confirmation or a "down-down" configuration, the elbows 118 of a single interconnecting member 116 extend circumferentially in the same direction (e.g., clockwise or counterclockwise). On the other hand, in an "up-down" or "down-up" configuration, the two elbows 118 of a single interconnecting member 116 extend to different sides (e.g., to the top and the bottom, or to the bottom and the top, respectively) of the elongate portion 120.

In the example of FIG. 1, each of the interconnecting members 116 is either in a "down-up" configuration or an "up-down" configuration. This is a conventional and prevailing design for many known stents. Additionally, in the example stent 110 of FIG. 1, there are half as many interconnecting members 116 disposed between any two adjacent rings 112 as there are repeating bent segments 122 in any single ring 112. This too is a common design feature for known stents. The stent 110 includes a cover (not shown, for clarity). The cover can be constructed from a biocompatible material (not shown) such as expanded polytetrafluoroethylene (ePFTE).

As described above, the conventional stent 110 is often associated with operational drawbacks, including foreshortening and recoil, especially when covered. Foreshortening is the property of a stent decreasing in length during expansion. Recoil is the property of a stent contracting from an expanded diameter to a partially expanded or non-expanded diameter. Foreshortening is particularly problematic, as it compromises the ability of the stent 110 to ensure correct placement and treatment of the stenosed vessel, and it also increases risk of damage to surrounding intima during expansion. Furthermore, recoil is associated with other risks, such as reduced reinforcement, which can lead to greater occlusion and blockage of the affected passageway. In general, poor efficacy of covered stents (e.g., as caused by substantial quantity of foreshortening and substantial quantity of recoil) has been proven in clinical settings to be linked with higher risk of restenosis. Thus, for a stent to be operable and safe for use, these negative characteristics must be eliminated, or at least maintained at acceptably low levels.

SUMMARY

There is a need for a stent device capable of being covered and having reduced foreshortening and recoil characteristics. The present invention is directed toward solutions to address this need, in addition to having other desirable characteristics that will be appreciated by one of skill in the art upon reading the present specification.

In accordance with an example embodiment of the present invention, a stent device is provided. The stent device includes a plurality of generally cylindrical rings each formed by a plurality of substantially repeating bent segments. Each of the plurality of bent segments includes one substantial peak, one substantial valley, and a transition region leading between the one substantial peak and the one substantial valley. Each bent segment has a midpoint on the transition region substantially midway between the one substantial peak and the one substantial valley. The plurality of rings are arranged in a series along a longitudinal axis in such a way that the one substantial peak and the one substantial valley of each bent segment of each ring in the series is substantially a mirror image of one substantial peak and one substantial valley of a corresponding curved segment in an immediately adjacent ring. A plurality of interconnecting members are included in the stent device, and each of the plurality of interconnecting members includes a first coupling end and a second coupling end opposite the first coupling end. An elongate portion extends between the first coupling end and the second coupling end. The first coupling end, the elongate portion, and the second coupling end combine in a first orientation or a second orientation that is substantially a mirror image of the first orientation. The first coupling end intersects with the midpoint of the transition region of a bent segment of a ring of the plurality of rings and the second coupling end intersects with the midpoint of a bent segment of a different and immediately adjacent ring of the plurality of rings. The plurality of interconnecting members are arranged in rows extending longitudinally along the device. Along each of the rows the interconnecting members alternate with each consecutive occurrence between the first orientation and the second orientation. The stent device further includes a cover disposed on the plurality of cylindrical rings and the plurality of interconnecting members.

In accordance with aspects of the present invention, the first coupling end and the second coupling end of each of the plurality of interconnecting members each can include an elbow. The number of interconnecting members between any two adjacent rings of the plurality of rings can be equal to the number of substantially repeating bent segments in each ring of the plurality of rings. The first coupling end and the second coupling end of each of the plurality of interconnecting members can be azimuthally aligned. The first coupling end and the second coupling end of each of the plurality of interconnecting members can be circumferentially aligned. Each of the plurality of rings can be independently expandable in a radial direction. The plurality of substantially repeating bent segments can form a generally sinusoidal pattern. A peak-to-valley amplitude quantity can be substantially equal for each of the plurality of rings. Each of the plurality of bent segments can have a substantially uniform width. All of the plurality of bent segments have substantially the same substantially uniform width. One or more of the plurality of interconnecting members can have a substantially non-uniform width.

In accordance with aspects of the present invention, the cover can include one or more cover materials, one or more coatings, or both. The cover can substantially cover an entirety of the plurality of rings. The cover can include expanded polytetrafluoroethylene (ePTFE). The plurality of rings can be constructed from one or more of a non-biodegradable alloy, stainless steel, or cobalt chromium, When the stent device with cover is expanded up to an operational deployment diameter, the stent device can exhibit a foreshortening of about 6% or less, about 3% or less, about 2% or less, about 1% or less, or about 0% or less. The stent device with cover can exhibit a foreshortening of about 0% when expanded up to an operational deployment diameter. The stent device with cover can exhibit a recoil of about 6.6% or less when the stent device with cover has an initial diameter of 1.6 mm and an expanded diameter of 5 mm. The stent device with cover can exhibit a recoil of about 7% or less when the covered stent has an initial diameter of 1.7 mm and an expanded diameter of 6 mm. The stent device with cover can exhibit a recoil of about 6.7% or less when the stent device with cover has an initial diameter of 1.8 mm and an expanded diameter of about 7 mm.

In accordance with an example embodiment of the present invention, a stent device is provided. The stent device includes a stent including a plurality of radially expandable rings arranged in a series along a common longitudinal axis and coupled together by a plurality of interconnecting members. Each of the plurality of radially expandable rings includes a plurality of substantially repeating bent segments. A cover formed of expanded polytetrafluoroethylene and including an inner layer and an outer layer can encapsulate the stent. When expanded to an operational deployment diameter, the stent device and cover can exhibit foreshortening of about 6% or less.

In accordance with aspects of the present invention, the stent device with cover can exhibit foreshortening of about 3% or less when expanded to an operational deployment diameter. The stent device with cover can exhibit foreshortening of about 2% or less when expanded to an operational deployment diameter. The stent device with cover can exhibit foreshortening of about 1% or less when expanded to an operational deployment diameter. The stent device with cover can exhibit foreshortening of about 0% or less when expanded to an operational deployment diameter.

In accordance with an example embodiment of the present invention, a method of manufacturing a stent device includes providing a plurality of generally cylindrical rings each formed by a plurality of substantially repeating bent segments. Each of the plurality of bent segments includes one substantial peak, one substantial valley, and a transition region leading between the one substantial peak and the one substantial valley. Each bent segment has a midpoint on the transition region substantially midway between the one substantial peak and the one substantial valley. The plurality of rings are arranged in a series along a longitudinal axis in such a way that the one substantial peak and the one substantial valley of each bent segment of each ring in the series is substantially a mirror image of one substantial peak and one substantial valley of a corresponding curved segment in an immediately adjacent ring. A plurality of interconnecting members are provided, and each of the plurality of interconnecting members including a first coupling end, a second coupling end opposite the first coupling end, and an elongate portion extending between the first coupling end and the second coupling end. The first coupling end, the elongate portion, and the second coupling end combine in a first orientation or a second orientation that is substantially a mirror image of the first orientation. A cover can be disposed on the plurality of cylindrical rings and the plurality of interconnecting members. The first coupling end intersects with the midpoint of the transition region of a bent segment of a ring of the plurality of rings and the second coupling end intersects with the midpoint of a bent segment of a different and immediately adjacent ring of the plurality of rings. The plurality of interconnecting members is arranged in rows extending longitudinally along the device. Along each of the rows, the interconnecting members alternate with each consecutive occurrence between the first orientation and the second orientation.

In accordance with further aspects of the present invention, the first coupling end and the second coupling end of each of the plurality of interconnecting members each can include an elbow. The number of interconnecting members between any two adjacent rings of the plurality of rings can be equal to the number of substantially repeating bent segments in each ring of the plurality of rings. The first coupling end and the second coupling end of each of the plurality of interconnecting members can be azimuthally aligned. The first coupling end and the second coupling end of each of the plurality of interconnecting members can be circumferentially aligned. Each of the plurality of rings can be independently expandable in a radial direction. The plurality of substantially repeating bent segments can form a generally sinusoidal pattern. A peak-to-valley amplitude quantity can be substantially equal for each of the plurality of rings. Each of the plurality of bent segments can have a substantially uniform width. All of the plurality of bent segments can have substantially the same substantially uniform width. One or more of the plurality of interconnecting members can have a substantially non-uniform width.

In accordance with further aspects of the present invention, the cover can substantially cover an entirety of a length of the plurality of rings. The cover can include expanded polytetrafluoroethylene (ePTFE). The cover can include one or more cover materials, or one or more coatings. The plurality of rings can be constructed from one or more of a non-biodegradable alloy, stainless steel, or cobalt chromium. The stent device with cover can be expanded up to an operational diameter then the stent device exhibits a foreshortening of about 6% or less, about 3% or less, about 2% or less, about 1% or less, or about 0% or less. The stent device with cover can exhibit a foreshortening of about 0% when expanded up to an operational diameter.

In accordance with an example embodiment of the present invention, a stent device is provided. The stent device includes a stent that includes a plurality of radially expandable rings arranged in a series along a common longitudinal axis and coupled by a plurality of interconnecting members. Each of the plurality of radially expandable rings includes a plurality of substantially repeating bent segments. The stent device can include a cover formed of expanded polytetrafluoroethylene. The cover includes an inner layer and an outer layer, and the cover encapsulates the stent. The stent device with cover exhibits foreshortening as indicated by a foreshortening curve shown in FIG. 7 or a foreshortening regime lying below a foreshortening curve shown in FIG. 7.

Figure 7:
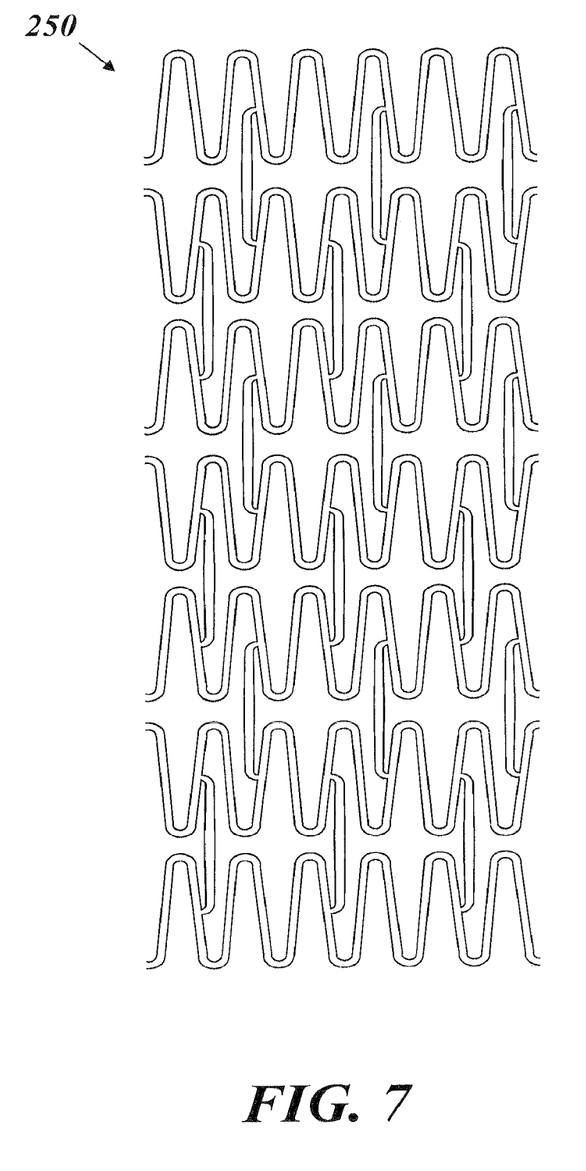
FIG. 7 is a flattened view of a stent similar in design to the stent of FIGS. 2 and 3, which was tested for purposes of comparison, according to aspects of the present invention.

In accordance with aspects of the present invention, the stent can have a length of about 24 mm or about 16 mm, and the stent device with cover can exhibit foreshortening as indicated by one of the foreshortening curves shown in FIG. 7.

Figure 3:
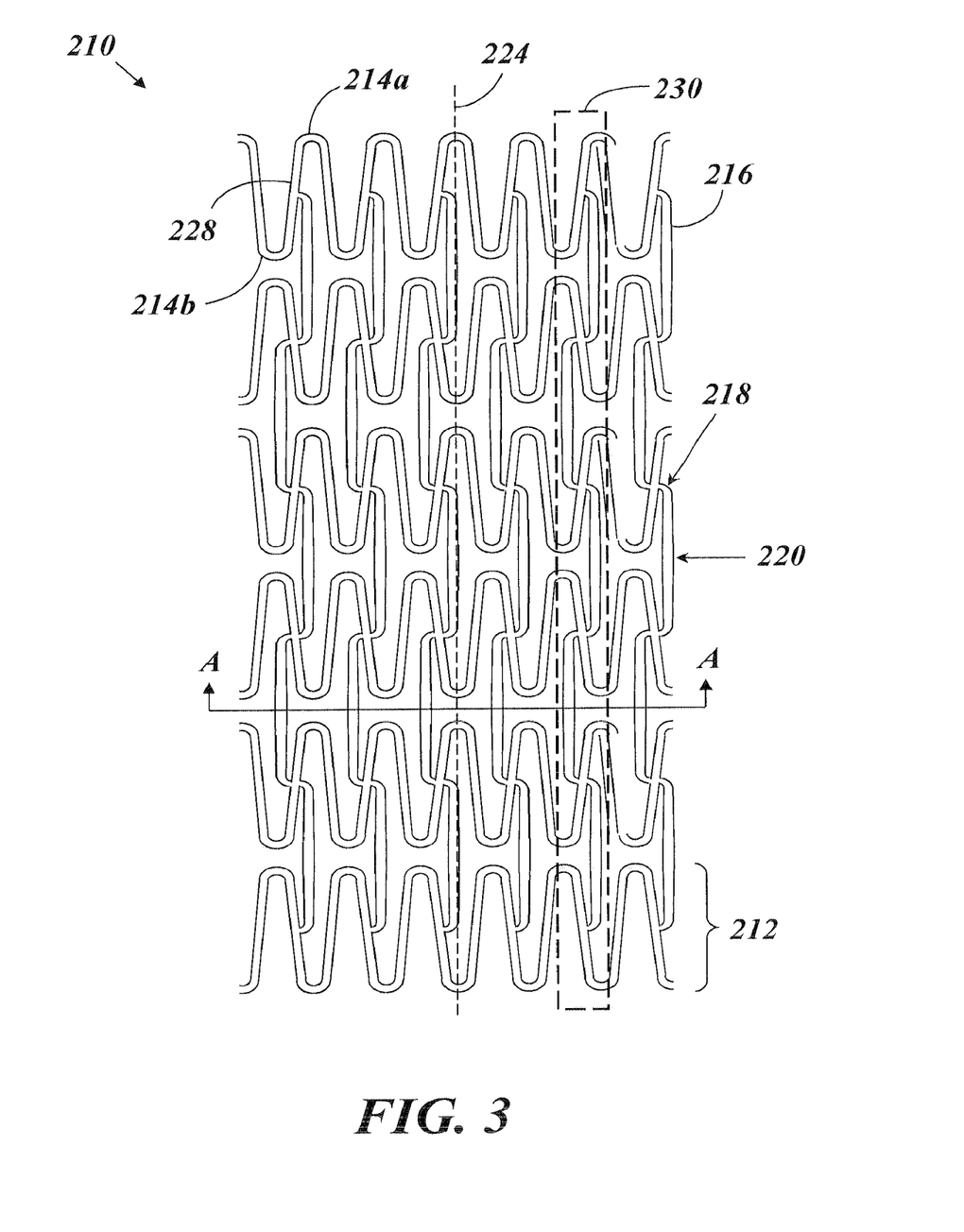
FIG. 3 is a flattened view of the example stent of FIG. 2, according to example embodiments of the present invention.

In accordance with aspects of the present invention, a stent device is provided that includes a plurality of radially expandable rings coupled together by a plurality of interconnecting members arranged as shown in FIG. 3.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to a stent having a structural design that greatly reduces foreshortening subsequent to or during expansion to an operational diameter. As supported herein by test results from sample stents according to embodiments of the present invention that were reduced to practice, foreshortening values of about 0% or less were achieved, while maintaining low values of recoil.

In particular, a stent according to an illustrative embodiment of the present invention can include a plurality of generally cylindrical rings, each formed of a plurality of substantially repeating bent segments. The rings can be arranged in a series along a longitudinal axis in such a way that each ring in the series is substantially a mirror image of an immediately adjacent ring. The rings can be interconnected by a plurality of interconnecting members, which can be arranged in rows that extend longitudinally along the stent. Each interconnecting member can include an elongate portion extending between two coupling ends. The interconnecting members can assume a first orientation or a second orientation that is substantially a mirror image of the first orientation. The interconnecting members can be coupled to the rings at midpoints of the bent segment. Along each row, consecutive interconnecting members alternate between the first orientation and the second orientation.

FIGS. 2 through 7, wherein like parts are designated by like reference numerals throughout, illustrate example embodiments of a stent and methods of making the same, according to the present invention. Although the present invention will be described with reference to the example embodiments illustrated in the figures, it should be understood that many alternative forms can embody the present invention. One of skill in the art will appreciate different ways to alter the parameters of the embodiments disclosed, such as the size, shape, or type of elements or materials, in a manner still in keeping with the spirit and scope of the present invention.

Figure 2:
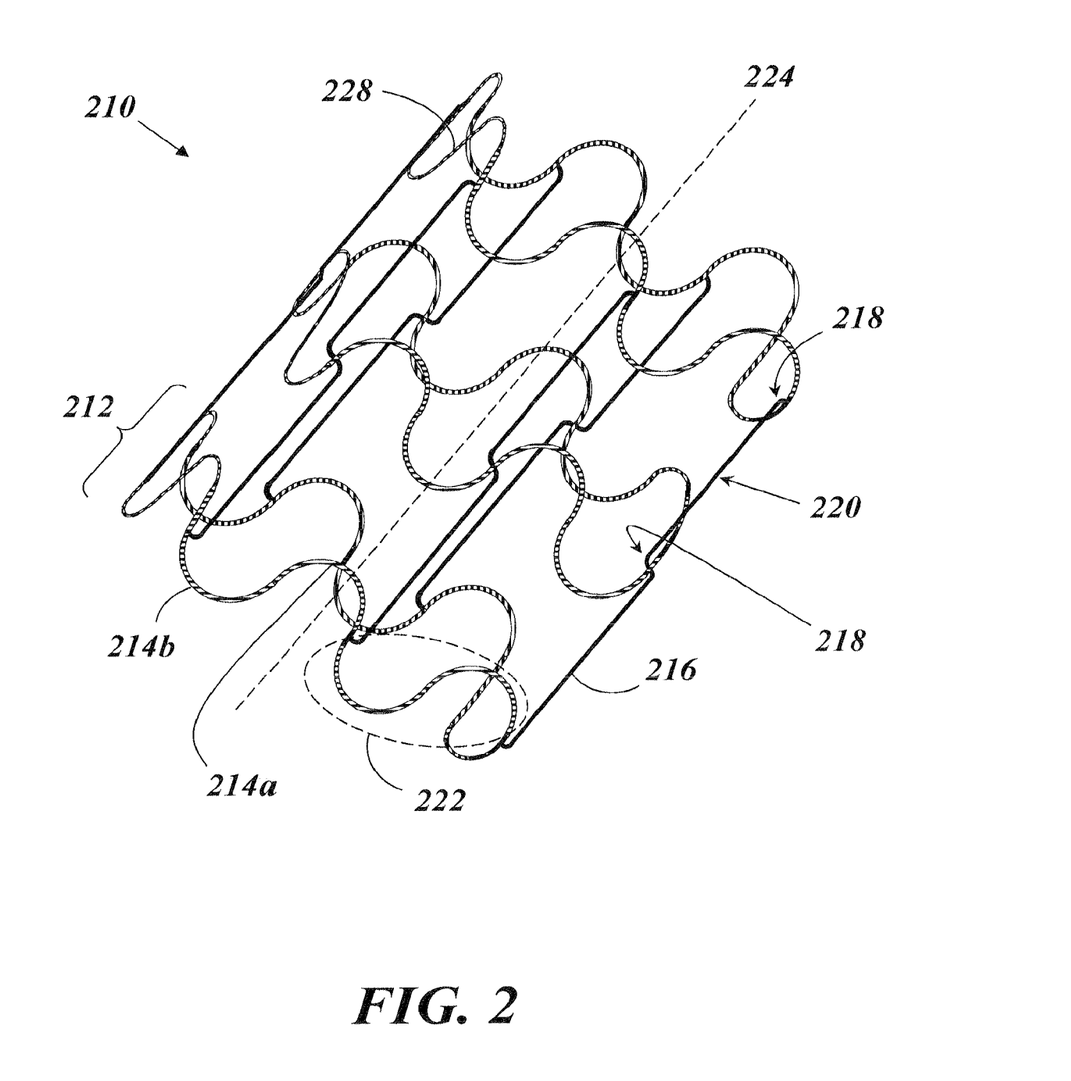
FIG. 2 is a perspective view of an example stent according to example embodiments of the present invention.

FIG. 2 depicts a perspective view of a stent 210 according to an example embodiment of the present invention. FIG. 3 depicts a top view of the stent 210 in a flattened (unrolled) state. The stent 210 includes a plurality of generally cylindrical, independently expandable rings 212 arranged in a series along a longitudinal axis 224. Each of the rings 212 can have a center point lying on the longitudinal axis 224, such that all of the rings 212 are coaxial. The plurality of rings 212 can collectively form an elongate, generally cylindrical shape. Each ring 212 includes a plurality of substantial peaks 214*a* and substantial valleys 214*b* arranged in an alternating fashion, such that each substantial peak 214*a* is adjacent two substantial valleys 214*b* and each substantial valley 214*b* is adjacent two substantial peaks 214*a*. A transition region 228 adjoins every substantial peak 214*a* to its adjacent valleys 214*b*, and adjoins every substantial valley 214*b* to its adjacent substantial peaks 214*a*. Accordingly, each substantial peak 214a is adjoined with a transition region 228 on each side, which leads to an adjacent substantial valley 214b. Similarly, each substantial valley 214b is adjoined with a transition region 228 on each side, which leads to an adjacent substantial peak 214a. The transition regions 228 can be unbent or bent. In FIG. 2, only three rings 212 are depicted for clarity. In FIG. 3, six rings 212 are illustrated. It will be appreciated by one of skill in the art that more or less rings 212 can be included in the stent 210.

In addition to substantial peaks 214a and substantial valleys 214b, the rings 212 are also formed of larger repeating units, herein referred to as substantially repeating bent segments 222. Each of the plurality of substantially repeating bent segments 222 includes one substantial peak 214a and one substantial valley 214b, and a transition region 228 adjoining the two. In the example embodiment of FIG. 2, the stent 210 includes six substantially repeating bent segments 222. However, fewer or greater numbers of substantially repeating bent segments 222 can be included depending on the particular intended application and dimensions of the target deployment site. It should be noted that the phrase "substantially repeating" in the present application is well understood by those of skill in the art to indicate that the units are repeating, but could accommodate a minor interruption in the repeating pattern. That is, the present invention is not intended to be limited to a strictly and exactly repeating pattern of bent segments. Should a stent be constructed that replicates the repeating bent segment pattern described and claimed herein, but for one or several minor interruptions to the pattern, such a stent would be considered to fall within the scope of the present invention.

In the example embodiment of FIGS. 2 and 3, each ring 212 is a mirror image of any ring 212 adjacent to it in the series. Accordingly, for any two adjacent rings 212, the substantial peaks 214a of one of the two adjacent rings 212 are circumferentially aligned with (e.g., are facing) the substantial valleys 214b of the other of the two adjacent rings 212, and vice versa. Said differently, the substantial peak 214a and the substantial valley 214b of each of the substantially repeating bent segments 222 are a mirror image of a substantial peak 214a and substantial valley 214b of a corresponding substantially repeating bent segment 222 of an immediately adjacent ring 212. In alternative embodiments, each successive ring 212 is not only a mirror image, but further is an angularly displaced mirror image. For example, each ring 212 can be "turned" relative to its adjacent rings 212 by some amount of angular displacement. The amount of angular displacement by which successive rings 212 are turned can be substantially uniform across the entire stent 210. In some embodiments, a covering process is used to cover the stent 210 which imparts a slight angular displacement to the successive rings 212.

The rings 212 are interconnected and fixedly secured to one another by a plurality of interconnecting members 216. Each interconnecting member 216 joins two adjacent rings 212. Each interconnecting member 216 includes two coupling ends 218 and an elongate portion 220. For each interconnecting member 216, the elongate portion 220 extends between and adjoins the two coupling ends 218. As one non-limiting example, the coupling ends 218 each can be an elbow (e.g., a generally "L" shaped member), as depicted in the example embodiment of FIGS. 2 and 3. Each coupling end 218 is adjoined with a ring 212 at a substantially repeating bent segment 222 at the midway point of a substantially repeating bent segment 222 (i.e., on the transition region 228 half way between the substantial peak 214a and the substantial valley 214b of a substantially repeating bent segment 222). For example, if the rings 212 generally form a sinusoidal shape defined by the equation $y=A*\sin(x)$, then the interconnecting members 216 can join with the rings 212 at the positions corresponding to zero-crossing points in the equation. The interconnecting members 216 and the rings 212 both can have a relatively thin, generally rectangular cross section (e.g., with rounded edges).

In contrast to the stent 110 of FIG. 1, each interconnecting member 216 of the stent 210 of FIGS. 2 and 3 is in an "up-up" configuration or a "down-down" configuration, such that the coupling ends 218 of a single interconnecting member 216 extend to the same side (e.g., to the top or the bottom, respectively) of the elongate portion 220, for substantially every interconnecting member 216 included in the stent 210. Said differently, the two coupling ends 218 of every individual interconnecting member 216 extend circumferentially in the same direction (e.g., clockwise or counter-clockwise). Furthermore, in the example embodiment of FIGS. 2 and 3, the number of interconnecting members 216 between any two adjacent rings 212 is equal to the number of substantially repeating bent segments 222 in each ring 212.

The two coupling ends 218 of each interconnecting member 216 of the example of FIGS. 2 and 3 are azimuthally or circumferentially aligned, such that a straight line connecting the two coupling ends 218 is parallel to the longitudinal axis 224. Accordingly, the two coupling ends 218 can be connected at corresponding mirror-image locations along substantially repeating bent segments 222 on adjacent rings 212. Furthermore, each interconnecting member 216 can be situated such that its length is substantially parallel to the longitudinal axis 224. The interconnecting members 216 form a plurality of rows 230 (see FIG. 3), each of which is substantially parallel to the longitudinal axis 224. The rows 230 extend longitudinally along the stent 210 and are equal in number to the number of substantially repeating bent segments 222 included in one ring 212.

The circumferential direction of orientation of the two coupling ends 218 of each interconnecting member 216 can vary for successive interconnecting members 216 along each row 230. In the example embodiment of FIGS. 2 and 3, the interconnecting members 216 of any single row 230 are arranged in an alternating fashion, such that the interconnecting members 216 alternate successively between the "up-up" configuration and the "down-down" configuration. Said differently, the directional orientation of the coupling ends 218 of successive interconnecting members 216 in a row 230 alternates between a first orientation wherein the coupling ends 218 point in a clockwise direction and a second orientation wherein the coupling ends 218 point in a counterclockwise direction. The first orientation and the second orientation (e.g., "up-up" and "down-down") are substantially mirror images of each other. In the example embodiment of FIG. 3, the interconnecting members 216 situated between any two adjacent rings 212 are all in the same configuration ("up-up" or "down-down"), such that all of the coupling ends 218 situated between any two adjacent rings 212 point in the same circumferential direction (e.g., clockwise or counter-clockwise).

Each of the interconnecting members 216 can have a variable, non-uniform width. Preliminary tests have suggested that such a feature of variable width of the interconnecting members 216 can strengthen the stent 210 and prevent foreshortening when deployed with a cover. For example, the elongate portion 220 can include a slight bulge at its center, such that the central width of the elongate portion 220 of the interconnecting members 216 is the widest position of the interconnecting member 216. In one example embodiment, the width at the center of the elongate portion 220 is about 1.5 times the size of the width at the coupling ends 218 of the interconnecting members 216. As further non-limiting example, the ratio of the largest width to the smallest width of the interconnecting members 216 can be about 1.56.

For each ring 212, each of the plurality of bent segments 222 can have a substantially uniform width. Furthermore, all substantial peaks 214a, substantial valleys 214b, and transition regions 228 of a ring 212 can have substantially the same substantially uniform width. It has been discovered that providing the substantially repeating bent segments 222 with the same uniform width does not increase the foreshortening of the stent 210 during expansion with a cover. This is beneficial because such uniform widths enable the stent 210 to achieve a smaller diameter and more uniform crimping into a prolapsed state.

In addition, the peak-to-valley amplitude is uniform across each ring 212. The peak-to-valley amplitude of each ring 212 can be uniform across all of the rings 212 or can vary across the rings 212. For example, two successive rings 212 in the stent 210 can have peak-to-valley amplitudes that are different from one another. The "peak-to-valley" amplitude is herein defined to have its normal definition as would be appreciated by one of skill in the art of the height of a substantially repeating bent segment 222 as measured vertically from the substantial peak 214a to the substantial valley 214b. It has been found that varying the peak-to-valley amplitude (e.g., varying the value of the peak-to-valley amplitude of the stent 210 or varying the peak-to-valley amplitude of particular rings 212 in the stent 210) can impact foreshortening characteristics of the stent 210. Thus, the peak-to-valley amplitude can be optimized as will be appreciated by one of skill in the art upon reading the present specification.

Figure 4:
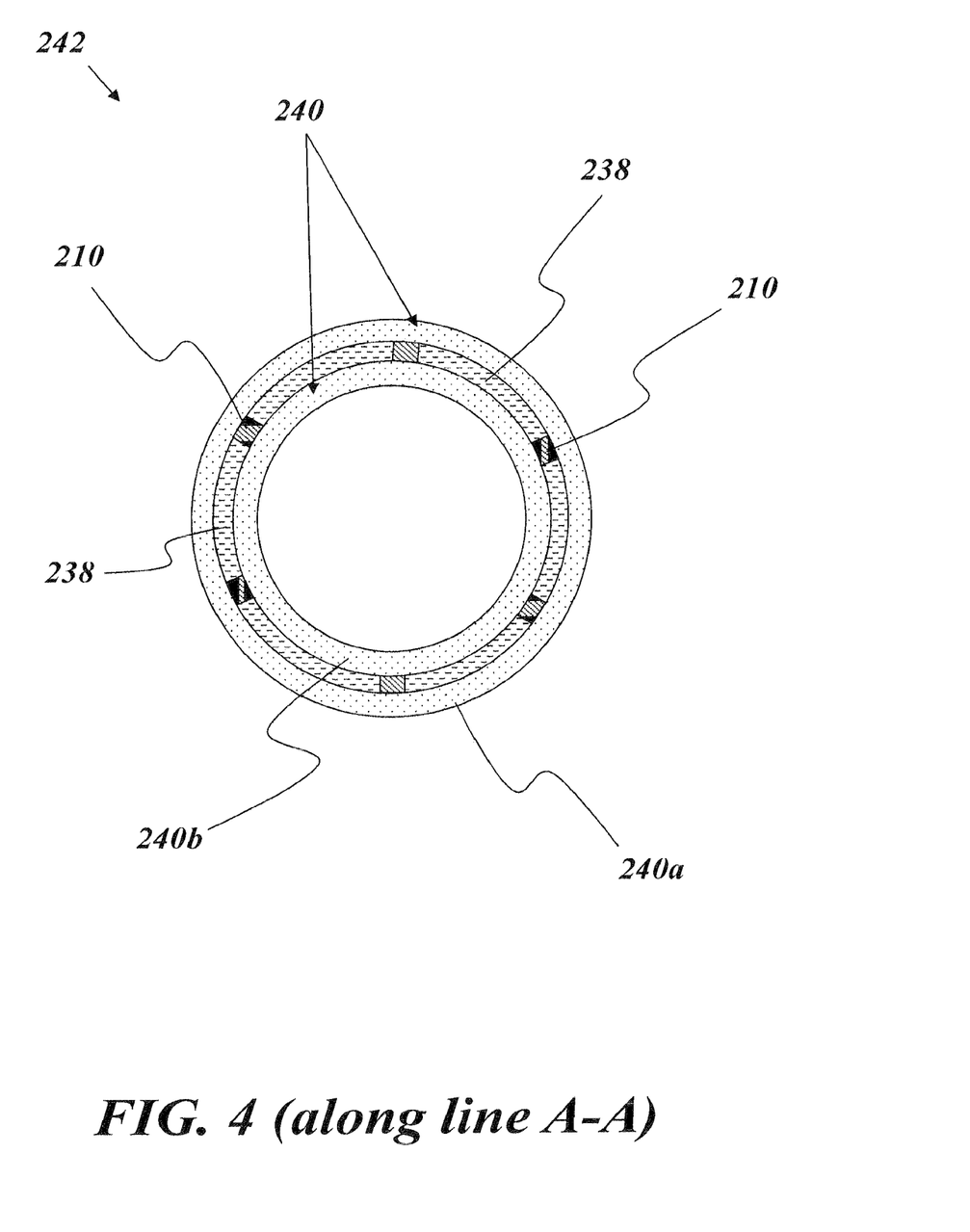
FIG. 4 is a cross sectional view of a covered stent device according to example embodiments of the present invention.

In accordance with one example embodiment of the present invention, the stent 210 is encapsulated in a cover, so as to form a covered stent device 242. For example, an illustrative embodiment of the covered stent device 242 is depicted in FIG. 4. More specifically, FIG. 4 depicts the stent 210 of FIG. 3 encapsulated in a cover 240 and depicted from a cross-sectional view along line A-A of FIG. 3. The cover 240 includes an outer layer 240a disposed on the exterior face of the stent 210 and an inner layer 240b disposed on an interior face of the stent 210. The outer and inner layers 240a, 240b are constructed of a single piece of material, e.g., which has been "cuffed" around the edge of the stent 210 so as to form the outer and inner layers 240a, 240b.

Figure 5:
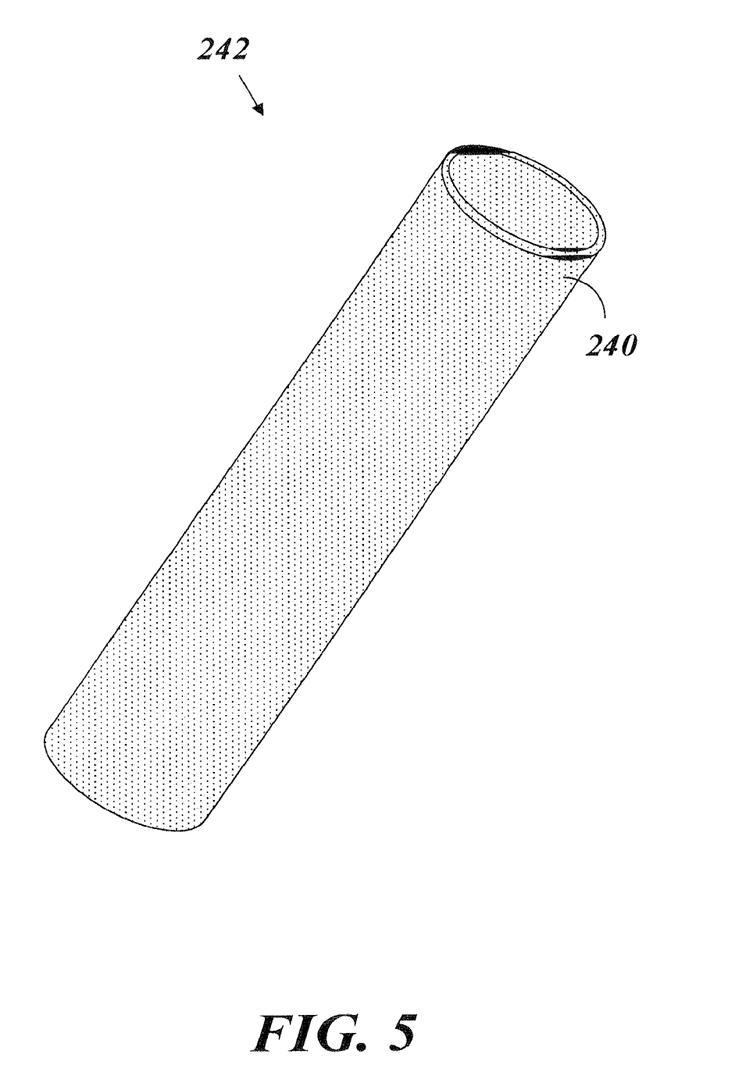
FIG. 5 is a perspective view of the covered stent device of FIG. 4 according to example embodiments of the present invention.

FIG. 5 depicts the covered stent device 242 of FIG. 4 from a perspective view. As can be seen, the stent 210 is hidden from view, as it is entirely encapsulated by the cover 240. The covered stent device 242 generally can be included in any number of different delivery devices and systems, e.g., for treatment of stenosed vessels. As just one non-limiting and illustrative example, the covered stent device 242 can be included in a balloon dilation catheter assembly, as will be readily appreciated by one of skill in the art.

Example 1

Figure 6:
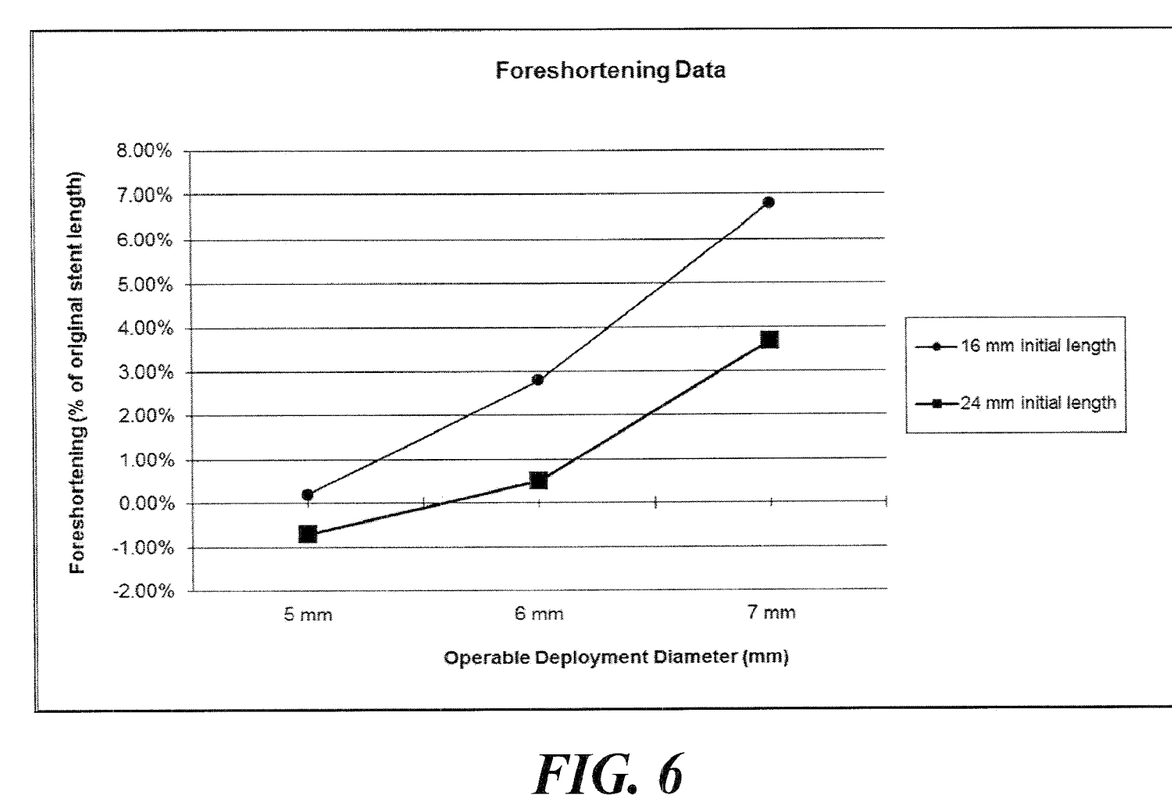
FIG. 6 is a graph depicting the median foreshortening values that were measured for various covered stent devices according to embodiments of the present invention that were built and tested.

An example of the covered stent device 242 that was built and tested will now be described with reference to FIG. 6. In particular, FIG. 6 depicts an example method that was used to build a plurality of covered stent devices 242. In the Example 1 provided herein, the cover 240 was constructed of expanded polytetrafluoroethylene (ePTFE).

The ePTFE cover was provided, having a desired diameter. The ePTFE cover was constructed according to conventional methods known to those of skill in the art (forming a PTFE tube, sintering the PTFE tube, etc.). The stent 210 according to FIGS. 2 and 3 was constructed and provided, having a desired diameter. The stent 210 was manufactured using conventional manufacturing techniques known to those in the art (laser cutting, electropolishing, etc.). In the example provided herein, the stent 210 was constructed from type 316 LVM stainless steel.

In the example provided herein, the small overlapping portion was situated near a center of the length of the stent 210. However, as described previously herein, the small overlapping portion alternatively can be situated at a position away from a center of the length. It has been found that displacing the overlapping portion from the center of the length of the stent 210 and nearer to one end of the stent 210 in this manner produces slower expansion of the resultant covered stent device at that particular end during deployment of the resultant covered stent device. Said differently, the small overlapping portion of the ePTFE cover can be used to restrict the expansion rate of portions of resultant covered stent device, e.g., thereby achieving greater timing control of expansion. Thus, depending on the particular geometry of the affected target site (e.g., of the intima and/or of the lesion being treated), it may be desirable in certain embodiments to position the overlapping portion of the ePTFE cover at a non-central longitudinal position so as to desirably affect the rate of expansion of the resultant covered stent device at that particular longitudinal position. In such embodiments, a non-central portion of the resultant covered stent device expands at a different (e.g., controlled or predetermined) rate or in a different amount than a remaining portion of the results covered stent device.

In particular, different groups of covered stent devices 242 were manufactured, generally distinguishable by length. In one group, a length of 16 mm was provided. In a second group, a length of 24 mm was utilized. The groups of stents were tested for performance characteristics, and their performance data was measured. This data is presented in Table I, below.

TABLE I

Foreshortening and Recoil Data

| Initial Diameter | Expanded Diameter* | Initial Length | Mean Foreshortening | Mean Recoil |
|---|---|---|---|---|
| 1.6 mm | 5 mm | 16 mm | 0.20% | 8.60% |
| 1.6 mm | 5 mm | 24 mm | −0.70% | 8.00% |
| 1.7 mm | 6 mm | 16 mm | 2.80% | 7.20% |
| 1.7 mm | 6 mm | 24 mm | 0.50% | 7.40% |
| 1.8 mm | 7 mm | 16 mm | 6.80% | 6.00% |
| 1.8 mm | 7 mm | 24 mm | 3.70% | 5.90% |

*indicates diameter to which the covered stent devices 242 were expanded and the diameter at which the covered stent devices 242 were measured for foreshortening and recoil results In general, all of the covered stent devices 242 represented in Table I, above, were constructed to include six substantially repeating bent segments 222 per ring 212. Each row in Table I represents data for a sample of fifteen substantially identical covered stent devices 242. The 16 mm covered stent devices 242 were constructed to include six rings 212. The 24 mm covered stent devices 242 were constructed to include nine rings 212. As presented in Table I, in some instances, foreshortening values of 0.20% were measured. In other instances, negative foreshortening values were measured, which indicate that the covered stent device 242 actually elongated during or upon expansion.

In all tests, the covered stent devices 242 were expanded to an operational deployment diameter. An "operational deployment diameter," as described herein, refers to a diameter at which the stent can be operably deployed (expanded) for at least one target site. The data of Table I are further presented in a graph in FIG. 6. Specifically, the graph of FIG. 6 displays the median values of foreshortening achieved for each covered stent device 242 as grouped by length. Accordingly, each foreshortening curve in FIG. 6 shows foreshortening characteristics exhibited for the covered stent devices 242 across a particular deployment diameter range for a particular initial length of the covered stent devices 242.

One of skill in the art will appreciate alternative ways to construct the covered stent devices 242 Furthermore, it should be understood that the dimensions selected for testing are illustrative and in no way limiting. Similarly, one of skill in the art will appreciate that the number of substantially repeating bent segments 222 to be included per ring 212 can depend on required crimping profiles, which depends on intended medical application, intended target sites, etc. The number of rings 212 to include can depend on the particular desired length. Still other features may be modified as will be appreciated by one of skill in the art upon reading the present specification.

In addition, many alternatives and modifications to the stent 210 are possible and will be appreciated by one of skill in the art. For example, rather than providing that all rings 212 of the stent 210 have the same substantially uniform peak-to-valley amplitude, one or more of the rings 212 can have a substantially uniform peak-to-valley amplitude that is different from the substantially uniform peak-to-valley amplitude of an adjacent ring 212. Still other alternatives are possible. However, one of skill in the art will appreciate that such alternatives (while acceptable and contemplated within the scope of the present invention) were not specifically tested and thus may not exhibit the described performance characteristics (e.g., recoil and/or foreshortening characteristics). Those of skill in the art will appreciate that seemingly minor structural differences in the lattice structure of a stent can have substantial impact on the operational and performance characteristics of that stent. As such, alternative designs to the structure described herein that are considered to fall within the scope of the present invention will have operational and performance characteristics similar to those of the present design.

Example 2

For comparative purposes, a plurality of comparative stents 250 having a slightly different structure from the stent 210 of FIGS. 2 and 3 were covered using the same methodology and subsequently tested for performance. Specifically, the design of the comparative stents 250 used in this example is depicted in FIG. 8 in a flattened, rolled-out state. To ensure that the comparative stents 250 provided for a fair comparison with the covered stent devices 242, the comparative stents 250 were tested for performance prior to covering, i.e., as bare metal stents. In particular, foreshortening and recoil of the comparative stents 250 when uncovered was measured. This data is presented in Table II, below. As can be seen, the comparative stents 250 performed with minimal foreshortening and recoil when uncovered and serving as bare metal stents. In particular, the average foreshortening values were as low as 1.1% in some instances.

TABLE II

Results for uncovered comparative stents 250

| Initial Diameter | Expanded Diameter* | Initial Length | Mean Foreshortening | Mean Recoil |
|---|---|---|---|---|
| 1.6 mm | 5 mm | 16 mm | 1.1% | 6.6% |
| 1.6 mm | 5 mm | 24 mm | −0.5% | 6.4% |
| 1.7 mm | 6 mm | 16 mm | 2.2% | 6.5% |
| 1.7 mm | 6 mm | 24 mm | 2.6% | 7.0% |
| 1.8 mm | 7 mm | 16 mm | 11.0% | 6.7% |

*indicates diameter to which stents were expanded and the diameter at which the uncovered comparative stents 250 were measured for foreshortening and recoil results Each row in Table II represents data for a sample of either two or three substantially identical comparative stents 250. Once the effectiveness of the design characterizing the comparative stents 250 was generally established (e.g., through the tests of the comparative stents 250 as bare metal stents), additional groups of the comparative stents 250 were covered using the same method. Subsequent to covering the comparative stents 250, the covered comparative stents 250 were subjected to the same foreshortening performance tests. In particular, foreshortening of the covered comparative stents 250 was measured. The resulting data is presented in Table III, below.

TABLE III

Results for covered comparative stents 250

| Initial Diameter | Expanded Diameter* | Initial Length | Mean Foreshortening |
|---|---|---|---|
| 1.6 mm | 5 mm | 16 mm | 7.74% |
| 1.6 mm | 5 mm | 24 mm | 6.03% |
| 1.7 mm | 6 mm | 16 mm | 17.17% |
| 1.7 mm | 6 mm | 24 mm | 13.08% |
| 1.8 mm | 7 mm | 16 mm | 29.64% |

*indicates diameter to which stents were expanded and the diameter at which the covered comparative stents 250 were measured for foreshortening results In the tests, the covered comparative stents 250 represented in Table III were expanded to an operational deployment diameter of about 5 mm, about 6 mm, or about 7 mm. Each row in Table III represents data for a sample of either fifteen or sixteen substantially identical covered comparative stents 250. As presented in Table III, mean foreshortening values of almost 30% were measured for the covered comparative stents 250 having an initial length of 16 mm that were expanded to a diameter of about 7 mm. For comparison, the 16 mm length stent design of the present invention utilized in Example 1 resulted in foreshortening values of about 6.8% when expanded to an operational deployment diameter of about 7 mm.

Thus, the stent design of the inventive covered stent devices 242 of Example 1 exhibited performance that demonstrated significantly less foreshortening amounts relative to the stent design of the example covered comparative stents 250 utilized in Example 2 when covered. These significantly different results were unexpected given the minor structural difference between the design of the covered comparative stents 250 and the design of the covered stent devices 242 according to embodiments of the present invention. As such, the data provided herein indicates that the covered stent devices 242 according to example embodiments of the present invention perform at surprising and unexpected performance levels (e.g., as measured by foreshortening). One of skill in the art will appreciate the data presented herein represents significant and notable improvement over the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

The invention claimed is:

1. A system for interconnecting members coupling a plurality of radially expandable rings of a stent device together, the system comprising:
a plurality of radially expandable rings;
a plurality of the interconnecting members, each of the interconnecting members comprising:
a first coupling end directly connected to a first one of the radially expandable rings;
a second coupling end opposite the first coupling end and directly connected to a second one of the radially expandable rings; and
an elongate portion connected between the first coupling end and the second coupling end, wherein the first coupling end, the elongate portion, and the second coupling end combine in a first orientation or a second orientation that is substantially a mirror image of the first orientation,
wherein each of the plurality of the interconnecting members has a fusiform shape in which a width of each interconnecting member at a center of the elongate portion is a widest position of each interconnecting member, wherein each interconnecting member narrows along its length in both directions from the center of the elongate portion, and wherein the first coupling end forms a first end of the fusiform shape and the second coupling end forms a second end of the fusiform shape.

2. The system of interconnecting members of claim 1, wherein the interconnecting members prevent a foreshortening of the stent device of more than 3% when the stent device is expanded to an operational deployment diameter.

3. The system of interconnecting members of claim 1, wherein the interconnecting members prevent a foreshortening of the stent device of more than 2% when the stent device is expanded to an operational deployment diameter.

4. The system of interconnecting members of claim 1, wherein the interconnecting members prevent a foreshortening of the stent device of more than 1% when the stent device is expanded to an operational deployment diameter.

5. The system of interconnecting members of claim 1, wherein the interconnecting members prevent a foreshortening of the stent device of more than 0% when the stent device is expanded to an operational deployment diameter.

6. The system of interconnecting members of claim 1, wherein the first and second coupling ends for each interconnecting member form as a pair of elbows that both extend circumferentially in a same direction about the stent device for that interconnecting member.

7. The system of interconnecting members of claim 1, wherein the first and second coupling ends for each interconnecting member form as a pair of elbows that are both azimuthally aligned, such that a straight line connecting each pair of elbows is parallel to a longitudinal axis of the stent device.

8. The system of interconnecting members of claim 1, wherein the elongate portion extends along a straight line parallel to a longitudinal axis of the stent device.

9. The system of interconnecting members of claim 1, wherein the plurality of interconnecting members is arranged in a plurality of rows extending longitudinally along the stent device, the interconnecting members of each row all arranged in one of the first or the second orientation, and the rows are arranged such that the interconnecting members in each consecutive one of the rows alternates between the first and second orientations.

10. The system of interconnecting members of claim 1, wherein the interconnecting members are encapsulated with a biocompatible material.

11. The system of interconnecting members of claim 10, wherein the biocompatible material is an expanded polytetrafluoroethylene (ePTFE) material.

12. An interconnecting member coupling a first ring and a second ring of a stent device, the interconnecting member comprising:
a first coupling end directly connected to the first ring;
a second coupling end opposite the first coupling end and directly connected to the second ring, the first and second coupling ends formed as a pair of elbows that: (i) both extend circumferentially about the stent device in a same direction and (ii) are both azimuthally aligned, such that a first straight line connecting each pair of elbows is parallel to a longitudinal axis of the stent device,
wherein the first ring and the second ring are radially expandable; and
an elongate portion connected between the first coupling end and the second coupling end and extending along a second straight line parallel to the longitudinal axis of the stent device,
wherein the interconnecting member has a fusiform shape in which a width of each interconnecting member at a center of the elongate portion is a widest position of each interconnecting member, wherein each interconnecting member narrows along its length in both directions from the center of the elongate portion, and wherein the first coupling end forms a first end of the fusiform shape and the second coupling end forms a second end of the fusiform shape.

\* \* \* \* \*